United States Patent
Fukazu et al.

(10) Patent No.: US 12,357,263 B2
(45) Date of Patent: Jul. 15, 2025

(54) MOBILE RADIOGRAPHIC IMAGING APPARATUS, CONTROL METHOD, AND RECORDING MEDIUM

(71) Applicant: Konica Minolta, Inc., Tokyo (JP)

(72) Inventors: Kosuke Fukazu, Kokubunji (JP); Nobuyuki Miyake, Yokohama (JP); Akira Hiroshige, Kokubunji (JP); Naoki Hayashi, Higashimurayama (JP)

(73) Assignee: Konica Minolta, Inc., Tokyo (JP)

( * ) Notice: Subject to any disclaimer, the term of this patent is extended or adjusted under 35 U.S.C. 154(b) by 258 days.

(21) Appl. No.: 18/312,775

(22) Filed: May 5, 2023

(65) Prior Publication Data
US 2023/0404516 A1 Dec. 21, 2023

(30) Foreign Application Priority Data
Jun. 17, 2022 (JP) .................. 2022-097695

(51) Int. Cl.
*A61B 6/00* (2024.01)
*G16H 30/20* (2018.01)
*G16H 40/63* (2018.01)
*H02J 7/00* (2006.01)

(52) U.S. Cl.
CPC .............. *A61B 6/56* (2013.01); *A61B 6/4405* (2013.01); *A61B 6/54* (2013.01); *G16H 30/20* (2018.01); *G16H 40/63* (2018.01); *H02J 7/0063* (2013.01)

(58) Field of Classification Search
CPC ......... A61B 6/548; A61B 6/54; A61B 66/542; A61B 2560/0214; A61B 6/586; A61B 9/56; A61B 8/54; A61B 18/10; H02J 7/00; H02J 7/0013; H02J 7/0014; H02J 7/0029; H02J 7/0031; H02J 7/0047; H02J 7/005; H02J 7/0063; H02J 7/007; H05G 1/30; H05G 1/56; H05G 1/58
See application file for complete search history.

(56) References Cited

FOREIGN PATENT DOCUMENTS

JP    2009153847 A    7/2009
WO    WO-2020217770 A1 * 10/2020 ............. G01T 1/175

* cited by examiner

*Primary Examiner* — Don K Wong
(74) *Attorney, Agent, or Firm* — BUCHANAN, INGERSOLL & ROONEY PC (57) ABSTRACT

A mobile radiographic imaging apparatus includes: two independent power supply units; two control devices each being driven with power supplied from each of the two power supply units; a first hardware processor in one of the two control devices includes; and a second hardware processor in the other one of the two control device. The first hardware processor inquires of the second hardware processor about a state of the other control device when a predetermined condition is satisfied, and shuts down the one control device or cancels shutdown of the one control device according to a response from the other control device.

6 Claims, 8 Drawing Sheets

MOBILE RADIOGRAPHIC IMAGING APPARATUS, CONTROL METHOD, AND RECORDING MEDIUM

CROSS-REFERENCE TO RELATED APPLICATIONS

The entire disclosure of Japanese Patent Application No. 2022-097695 filed on Jun. 17, 2022 is incorporated herein by reference in its entirety.

TECHNICAL FIELD

The present invention relates to a mobile radiographic imaging apparatus, a control method, and a recording medium.

DESCRIPTION OF THE RELATED ART

There is known a mobile radiographic imaging apparatus intended to perform radiographic imaging outside (in hospital room, operating room, and the like) an imaging room in a hospital. The mobile radiographic imaging apparatus needs to be driven by a battery because the mobile radiographic imaging apparatus can be moved to any place.

For example, in order to prevent forgetting to charge the battery of a mobile X-ray imaging apparatus, a technique has been proposed in which a computer that controls each unit of the apparatus can shut down its own system when it is detected that a charger has been connected to an external power supply (see JP 2009-153847 A).

The mobile radiographic imaging apparatus includes a DR (digital radiography) console for performing a setting operation for radiation detection of an FPD (flat panel detector) panel. If an independent power supply is not provided for the DR console (single power supply configuration), the DR console is shut down when turning off the power for the entire apparatus. In the single power supply configuration, since there is one power supply for turning on/off the apparatus, the operation is simple. However, the apparatus cannot be activated by the DR console alone.

On the other hand, a system (dual power supply configuration) is also known in which an apparatus main power supply for supplying power for operations related to radiation emission and apparatus driving (movement/traveling of apparatus, movement of irradiator, adjustment of irradiation field, and the like) and a DR power supply for supplying power to the DR console are independently driven. In the dual power supply configuration, the apparatus main power supply and the DR power supply are turned on/off independently. Therefore, by selectively turning off an unused power system, for example, by performing an operation related to a captured image (brightness adjustment, output to external device, and the like) in a state in which the apparatus main power supply is turned off and only the DR power supply is turned on or by performing movement/traveling of the apparatus in a state in which the DR power supply is turned off and only the apparatus main power supply is turned on, the battery can be used efficiently (saving power consumption). In addition, since patient information or captured images are displayed on the DR console, turning off the DR power supply also has an advantage that it is difficult for third parties to see the privacy information.

SUMMARY OF THE INVENTION

However, in the mobile radiographic imaging apparatus with a dual power supply configuration (system in which apparatus main power supply and DR power supply are independent of each other), if the user forgets to turn off at least one of the power supplies, there is a risk that the data will be corrupted due to forced termination due to insufficient battery power or the battery will deteriorate due to long-term driving. In addition, when power is being supplied to a peripheral device from any of the power supplies, the peripheral device will continue to operate until the power supply is turned off.

Therefore, when each power supply in the dual power supply configuration can be turned off, it is desirable to turn off the power supply as appropriate without relying on the user's operation.

By the way, when the technique described in JP 2009-153847 A is applied to the mobile radiographic imaging apparatus with a dual power supply configuration, even though a large-capacity captured image is being transmitted to the outside, the mobile radiographic imaging apparatus can be shut down on the condition that the mobile radiographic imaging apparatus is connected to an external power supply (on the condition that the mobile radiographic imaging apparatus is being charged). Thus, when shutting down the apparatus, it is necessary to consider not only the state of power supply to the apparatus but also the processing state of the apparatus.

In the case of the dual power supply configuration, a method is also conceivable in which the DR console periodically inquires of the main body of the apparatus (a part responsible for radiation emission or movement/traveling of the apparatus) about whether or not the apparatus is in operation (checks whether or not the apparatus is in use) and the DR console is shut down if there is no response indicating that the apparatus is in operation from the main body of the apparatus. However, the mobile radiographic imaging apparatus has a limited power supply capacity. Therefore, if power consumption increases due to frequent inquiries from the DR console to the main body of the apparatus, there is a risk that the battery will run out during actual rounds.

The present invention has been made in view of the aforementioned problems in the related art, and it is an object of the present invention to achieve both efficient power consumption and user's convenience in a mobile radiographic imaging apparatus having two independent power supply units.

To achieve at least one of the abovementioned objects, according to an aspect of the present invention, a mobile radiographic imaging apparatus reflecting one aspect of the present invention is a mobile radiographic imaging apparatus including: two independent power supply units; two control devices each being driven with power supplied from each of the two power supply units; a first hardware processor in one of the two control devices includes; and a second hardware processor in the other one of the two control device. The first hardware processor inquires of the second hardware processor about a state of the other control device when a predetermined condition is satisfied, and shuts down the one control device or cancels shutdown of the one control device according to a response from the other control device.

To achieve at least one of the abovementioned objects, according to an aspect of the present invention, a control method reflecting one aspect of the present invention is a control method for a mobile radiographic imaging apparatus including two independent power supply units and two control devices each being driven with power supplied from each of the two power supply units. The control method includes: causing a first hardware processor of one of the two control devices to inquire of a second hardware processor of the other one of the two control devices about a state of the other control device when a predetermined condition is satisfied and to shut down the one control device or cancel shutdown of the one control device according to a response from the other control device.

To achieve at least one of the abovementioned objects, according to an aspect of the present invention, a recording medium reflecting one aspect of the present invention is a non-transitory recording medium storing a computer readable program causing a computer of one of two control devices of a mobile radiographic imaging apparatus including two independent power supply units and the two control devices each being driven with power supplied from each of the two power supply units to execute: inquiring of the other one of the two control devices about a state of the other control device when a predetermined condition is satisfied; and shutting down the one control device or canceling shutdown of the one control device according to a response from the other control device.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION

Hereinafter, one or more embodiments of the present invention will be described with reference to the drawings. However, the scope of the invention is not limited to the disclosed embodiments.

FIRST EMBODIMENT

First, a first embodiment of the present invention will be described.

Figure 1:
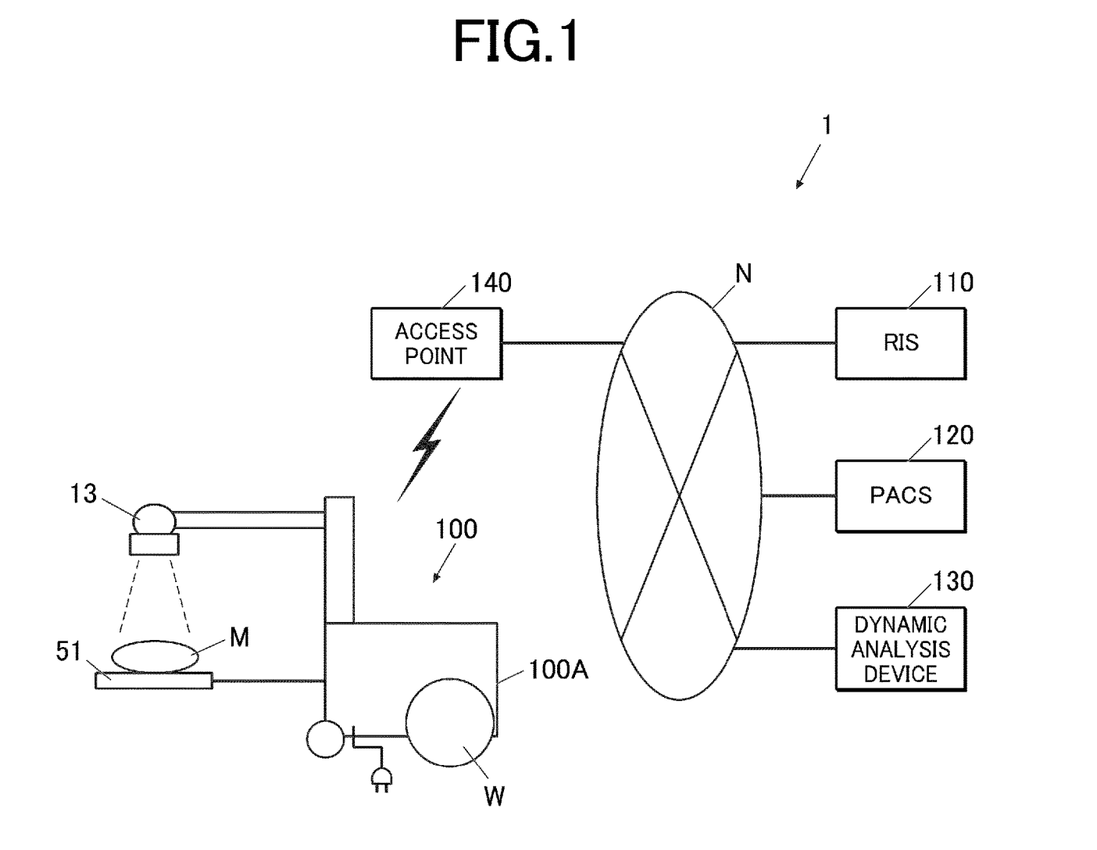
FIG. 1 is a diagram showing an overall configuration example of a radiographic imaging system according to a first embodiment of the present invention.

FIG. 1 shows an example of the overall configuration of a radiographic imaging system 1. The radiographic imaging system 1 is a system built in a medical facility. As shown in FIG. 1, the radiographic imaging system 1 is configured such that a mobile radiographic imaging apparatus 100, an RIS (radiology information system) 110, a PACS (picture archiving and communication system) 120, and a dynamic analysis device 130 are connected to each other through a communication network N, such as a LAN (local area network) or a WAN (wide area network), so as to be able to transmit and receive data therebetween. In the medical facility where the radiographic imaging system 1 is installed, a plurality of access points 140 are provided. The mobile radiographic imaging apparatus 100 can be connected to the communication network N through the access point 140 by wireless LAN communication using a wireless LAN interface provided in the mobile radiographic imaging apparatus 100. The mobile radiographic imaging apparatus 100 may have a wired LAN interface in addition to the wireless LAN interface. In this case, the mobile radiographic imaging apparatus 100 can be connected to the communication network N by wired LAN communication using a wired LAN interface.

Each apparatus configuring the radiographic imaging system 1 conforms to the DICOM (digital image and communications in medicine) standard, and communication between apparatuses is performed according to the DICOM.

The mobile radiographic imaging apparatus 100 is, for example, an apparatus for performing radiographic imaging of a patient, who is difficult to move, when making rounds. The mobile radiographic imaging apparatus 100 has wheels W on a main body 100A, and is configured as a movable rounds car.

The mobile radiographic imaging apparatus 100 is brought into an operating room, an intensive care unit (ICU), a hospital room, or the like, and performs still image capturing or dynamic imaging of a subject M by emitting radiation from a radiation generator 13 in a state in which an FPD 51 is placed between the subject M lying on a bed and the bed or inserted into an insertion port provided on a surface of the bed opposite to the subject M, for example. In the present embodiment, the still image capturing refers to acquiring one image of the subject M in response to one imaging operation. The dynamic imaging refers to acquiring a plurality of images of the subject M by repeatedly emitting radiation, such as X-rays, to the subject M in a pulsed manner at predetermined time intervals in response to one imaging operation (pulse irradiation) or by continuously emitting radiation, such asX-rays, to the subject M at a low dose rate without interruption in response to one imaging operation (continuous irradiation). A series of images obtained by dynamic imaging are called a dynamic image. Each of the plurality of images forming the dynamic image is called a frame image.

The dynamic imaging includes moving image capturing, but does not include capturing a still image while displaying a moving image. The dynamic image includes a moving image, but does not include an image obtained by capturing a still image while displaying a moving image.

The RIS 110 issues and stores examination order information, and transmits the issued examination order information to the mobile radiographic imaging apparatus 100 through the communication network N.

The PACS 120 is an image management device that stores and manages medical images (still images and dynamic images) generated by a modality, such as the mobile radiographic imaging apparatus 100, or analysis results by the dynamic analysis device 130 in association with patient information and examination information.

The dynamic analysis device 130 performs analysis processing on the dynamic image output from the mobile radiographic imaging apparatus 100, and transmits the dynamic image and the analysis result to the PACS 120. The dynamic analysis device 130 can perform a plurality of types of analysis processing, and performs a designated type of analysis processing among the plurality of types of analysis processing.

Figure 2:
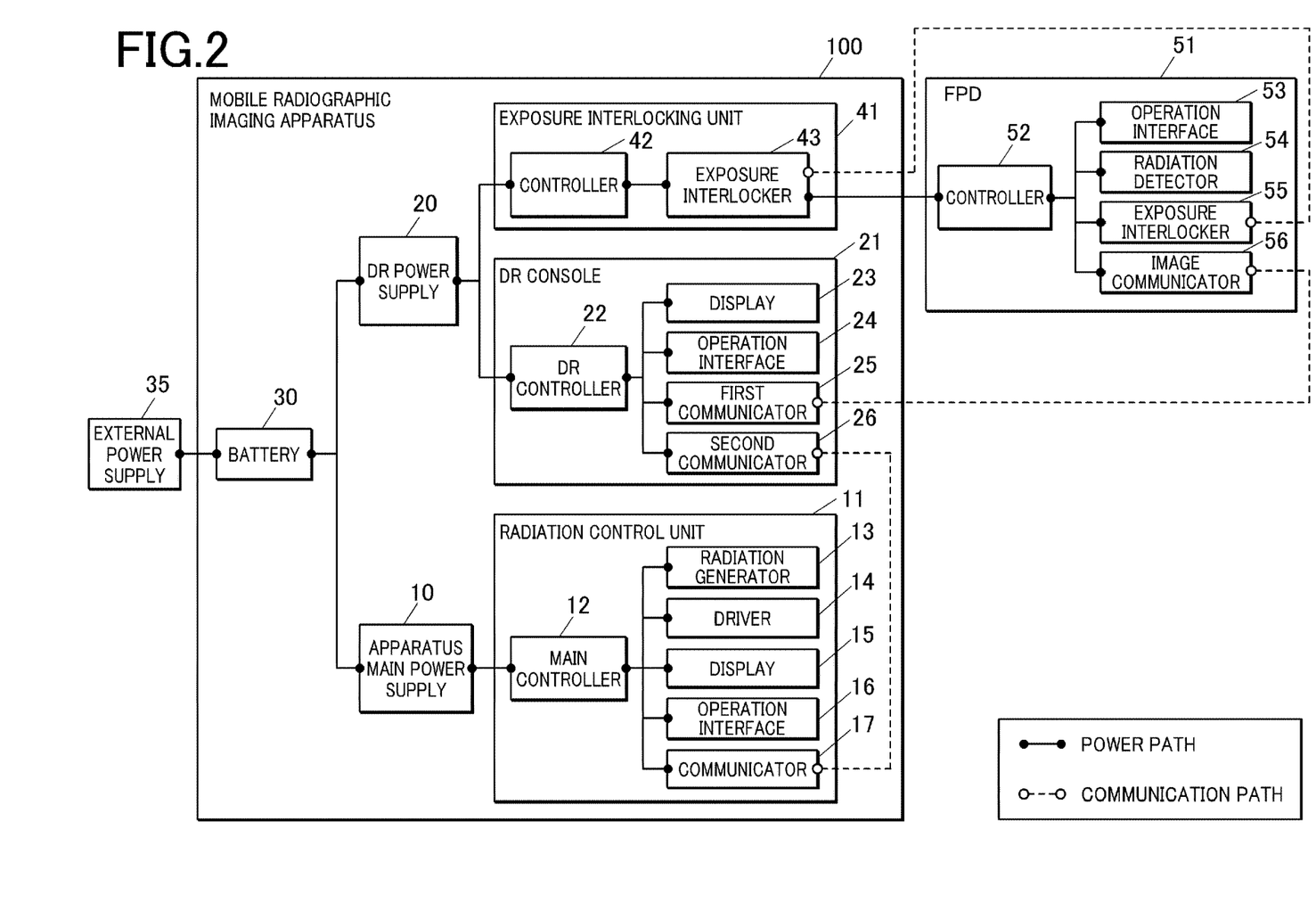
FIG. 2 is a block diagram showing the functional configuration of a mobile radiographic imaging apparatus.

FIG. 2 is a block diagram showing the functional configuration of the mobile radiographic imaging apparatus 100 (rounds car). As shown in FIG. 2, the mobile radiographic imaging apparatus 100 includes an apparatus main power supply 10, a radiation control unit 11, a DR power supply 20, a DR console 21, a battery 30, an exposure interlocking unit 41, and the like.

The apparatus main power supply 10 and the DR power supply 20 are power supply units independent of each other. That is, the mobile radiographic imaging apparatus 100 is a mobile radiographic imaging apparatus having a dual power supply configuration.

The apparatus main power supply 10 supplies power to the radiation control unit 11.

The DR power supply 20 supplies power to the DR console 21 and the exposure interlocking unit 41. The DR power supply 20 supplies power to the FPD 51 through the exposure interlocking unit 41.

The radiation control unit 11 is driven with the power supplied from the apparatus main power supply 10. The radiation control unit 11 is a control device that controls functional units related to radiation emission and operations (movement/traveling of apparatus, movement of irradiator, adjustment of irradiation field, and the like) for driving the mobile radiographic imaging apparatus 100. The radiation control unit 11 includes a main controller 12 (second hardware processor), a radiation generator 13, a driver 14, a display 15, an operation interface 16, a communicator 17, and the like.

The main controller 12 is configured to include a CPU (central processing unit), a RAM (random access memory), a ROM (read only memory), and the like. The CPU of the main controller 12 centrally controls the operation of each unit of the radiation control unit 11 and the apparatus main power supply 10 by reading various programs stored in the ROM, loading the programs to the RAM, and performing various processes according to the loaded programs.

The radiation generator 13 has a rotating anode, a filament, and the like, and generates radiation according to irradiation conditions (conditions related to radiation emission, such as tube voltage, tube current, irradiation time, and current-time product). The radiation generator 13 emits radiation to the subject M from a position facing the FPD 51 with the subject M interposed therebetween.

The driver 14 drives a motor to rotate the wheels W based on a control signal from the main controller 12. In addition, the driver 14 moves the radiation generator 13 or adjusts the irradiation field.

The display 15 is configured by a monitor, such as an LCD (liquid crystal display), and displays various screens according to the instruction of a display signal input from the main controller 12 or a DR controller 22. For example, the display 15 displays the irradiation conditions and the like.

The operation interface 16 includes operation buttons, a touch panel, and the like, and detects the content of the user's operation and inputs the operation content to the display 15 as operation information or outputs the operation content to the main controller 12.

As the user's operation, for example, changing the irradiation conditions can be mentioned. In addition, the operation interface 16 includes a handlebar for traveling or a handle for moving the radiation generator 13, and detects the users handle operation and transmits the detection result to the main controller 12 as operation information. Based on the operation information, the main controller 12 controls the driver 14 through a control signal as described above.

The communicator 17 is an interface for transmitting and receiving data to and from the DR console 21. For example, the communicator 17 transmits the irradiation conditions to the DR console 21.

The DR console 21 is driven with the power supplied from the DR power supply 20. The DR console 21 is a control device that controls functional units related to radiation detection and operations (brightness adjustment, output to external device, and the like) on captured images. The DR console 21 includes the DR controller 22 (first hardware processor), a display 23, an operation interface 24, a first communicator 25, a second communicator 26, and the like.

The DR controller 22 is configured to include a CPU, a RAM, a ROM, and the like. The CPU of the DR controller 22 centrally controls the operation of each unit of the DR console 21 and the DR power supply 20 by reading various programs stored in the ROM, loading the programs to the RAM, and performing various processes according to the loaded programs.

The display 23 is configured by a monitor, such as an LCD (liquid crystal display), and displays various screens according to the instruction of a display signal input from the DR controller 22. For example, the display 23 displays patient information of a patient to be imaged, a captured image, and the like.

The operation interface 24 includes operation buttons, a touch panel, and the like, and detects the content of the user's operation (type of operation button pressed, contact position of finger or touch pen, and the like) and outputs the operation content to the DR controller 22 as operation information.

As the users operation, for example, adjusting the brightness of a captured image and outputting the captured image to an external device can be mentioned.

The first communicator 25 is an interface for transmitting and receiving data to and from the FPD 51 by wireless communication. For example, the first communicator 25 receives image data of a captured image from the FPD 51.

In addition, the first communicator 25 is an interface that is connected to the access point 140 through a wireless LAN interface and transmits and receives (inputs and outputs) data to and from external devices (RIS 110, PACS 120, dynamic analysis device 130, and the like) connected to the communication network N through the access point 140. For example, the first communicator 25 transmits the image data of a captured image to an external device. The first communicator 25 may transmit and receive data to and from an external device connected to the communication network N through a wired LAN. Alternatively, the first communicator 25 may have both a wireless LAN interface and a wired LAN interface. In this case, one of the wireless LAN interface and the wired LAN interface may be used exclusively to transmit and receive data to and from an external device, or both the wireless LAN interface and the wired LAN interface may be used simultaneously to transmit and receive data to and from an external device.

The second communicator 26 is an interface for transmitting and receiving data to and from the radiation control unit 11. For example, the second communicator 26 receives the irradiation conditions from the radiation control unit 11.

The battery 30 stores power supplied from an external power supply 35, and supplies the stored power to the apparatus main power supply 10 or the DR power supply 20. The battery 30 is connected to a power cable having a plug at its distal end, and can receive the power supplied from the external power supply 35 by insetting the plug into a nearby outlet. When the battery 30 is not connected to the external power supply 35, the remaining amount of the battery 30 decreases with the use of the apparatus main power supply 10 or the DR power supply 20.

The exposure interlocking unit 41 synchronizes the operation timing of the radiation generator 13 of the radiation control unit 11 and the operation timing of a radiation detector 54 of the FPD 51. The exposure interlocking unit 41 includes a controller 42, an exposure interlocker 43, and the like.

The controller 42 is configured to include a CPU, a RAM, a ROM, and the like. The CPU of the controller 42 centrally controls the operation of each unit of the exposure interlocking unit 41 by reading various programs stored in the ROM, loading the programs to the RAM, and performing various processes according to the loaded programs.

The exposure interlocker 43 transmits an exposure interlocking signal to the FPD 51 based on the irradiation conditions transmitted from the radiation control unit 11 and acquired through the DR console 21.

The FPD 51 includes a controller 52, an operation interface 53, a radiation detector 54, an exposure interlocker 55, an image communicator 56, and the like.

The controller 52 is configured to include a CPU, a RAM, a ROM, and the like. The CPU of the controller 52 centrally controls the operation of each unit of the FPD 51 by reading various programs stored in the ROM, loading the programs to the RAM, and performing various processes according to the loaded programs.

The operation interface 53 includes operation buttons and the like, and detects the content of the user's operation and outputs the operation content to the controller 52 as operation information.

As the user's operation, for example, switching the imaging mode can be mentioned.

The radiation detector 54 has a glass substrate and the like, and is formed by arranging a plurality of detection elements (pixels), which detect radiation emitted from the radiation generator 13 and transmitted through at least the subject M according to its intensity and convert the detected radiation into an electrical signal and accumulate the electrical signal, in a matrix at predetermined positions on the substrate. Each pixel includes a switcher, such as a TFT (thin film transistor). Types of the radiation detector 54 include an indirect conversion type in which radiation is converted into an electrical signal by a photoelectric conversion element through a scintillator and a direct conversion type in which radiation is directly converted into an electrical signal, and either type may be used.

The exposure interlocker 55 interlocks the operation of the radiation detector 54 with the operation of the radiation generator 13 of the radiation control unit 11 based on the exposure interlocking signal transmitted from the exposure interlocking unit 41.

The image communicator 56 is an interface for transmitting and receiving data to and from the DR console 21 by wireless communication. For example, the image communicator 56 transmits the image data of a radiographic image obtained by the radiation detector 54 to the DR console 21.

The DR console 21 (one control device) inquires of the radiation control unit 11 (the other control device) about the state of the radiation control unit 11 when a predetermined condition is satisfied. The predetermined condition is a condition (termination condition) for shutting down the DR console 21 and terminating the DR power supply 20. For example, as the predetermined condition, "a state in which no operation has been performed on the DR console 21 continues for a predetermined time or longer" can be mentioned.

The DR console 21 shuts down the DR console 21 or cancels the shutdown of the DR console 21 according to the response from the radiation control unit 11.

The DR console 21 transmits a shutdown request to the radiation control unit 11 or a peripheral device connected to the DR console 21 before shutting down the DR console 21.

In the mobile radiographic imaging apparatus 100, imaging based on the examination order information is performed under the control of the main controller 12 and the DR controller 22. The FPD 51 transmits a captured image obtained by the imaging to the mobile radiographic imaging apparatus 100 (DR console 21) through the image communicator 56. When the imaging ends, the DR controller 22 of the DR console 21 receives the captured image transmitted from the FPD 51 through the first communicator 25 and temporarily stores the captured image in the RAM, and outputs the captured image to external devices (PACS 120, dynamic analysis device 130, and the like) through the first communicator 25 (transmission of image data).

Next, the operation of the mobile radiographic imaging apparatus 100 will be described.

Figure 3:
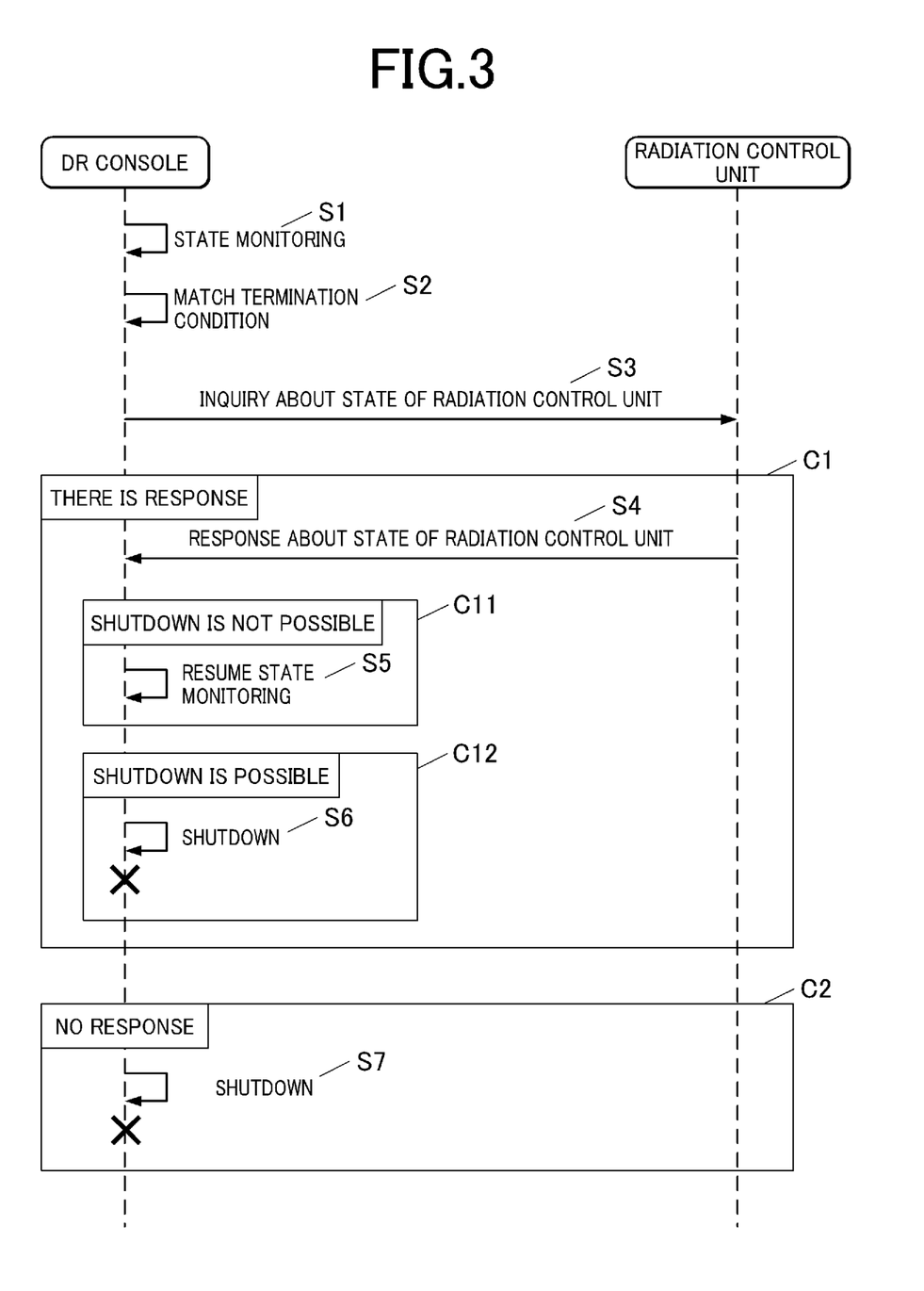
FIG. 3 is a sequence diagram of power shutdown processing performed in a DR console and a radiation control unit.

FIG. 3 is a sequence diagram of power shutdown processing performed in the DR console 21 and the radiation control unit 11.

The DR controller 22 of the DR console 21 monitors the state of the DR console 21 (step S1).

When the termination condition of the DR console 21 is satisfied (step S2), the DR controller 22 transmits an inquiry to the radiation control unit 11 through the second communicator 26 to check the state of the radiation control unit 11 (step S3). The "state of the radiation control unit 11" subject to inquiry includes the operation state of the radiation control unit 11 (whether or not the radiation control unit 11 is in operation), the termination state of the radiation control unit 11 (whether or not the operation of the radiation control unit 11 has ended), an input state (whether or not an operation input/data input is being performed), an exposure state (whether or not radiation is being emitted from the radiation generator 13), a traveling state (whether or not the mobile radiographic imaging apparatus 100 is traveling), and the like.

When the DR console 21 receives a response to the inquiry about the state of the radiation control unit 11 from the radiation control unit 11 (case C1, step S4), the DR controller 22 of the DR console 21 determines whether or not the DR console 21 can be shut down according to the response from the radiation control unit 11.

If shutdown is not possible (case C11), the DR controller 22 resumes monitoring the state of the DR console 21 (step S5). That is, the DR controller 22 cancels the shutdown of the DR console 21.

If shutdown is possible (case C12), the DR controller 22 shuts down the DR console 21 and turns off the DR power supply 20 (step S6).

When the DR console 21 does not receive any response to the inquiry about the state of the radiation control unit 11 from the radiation control unit 11 (case C2), the DR controller 22 shuts down the DR console 21 and turns of the DR power supply 20 (step S7).

As described above, the power shutdown processing ends.

Figure 4:
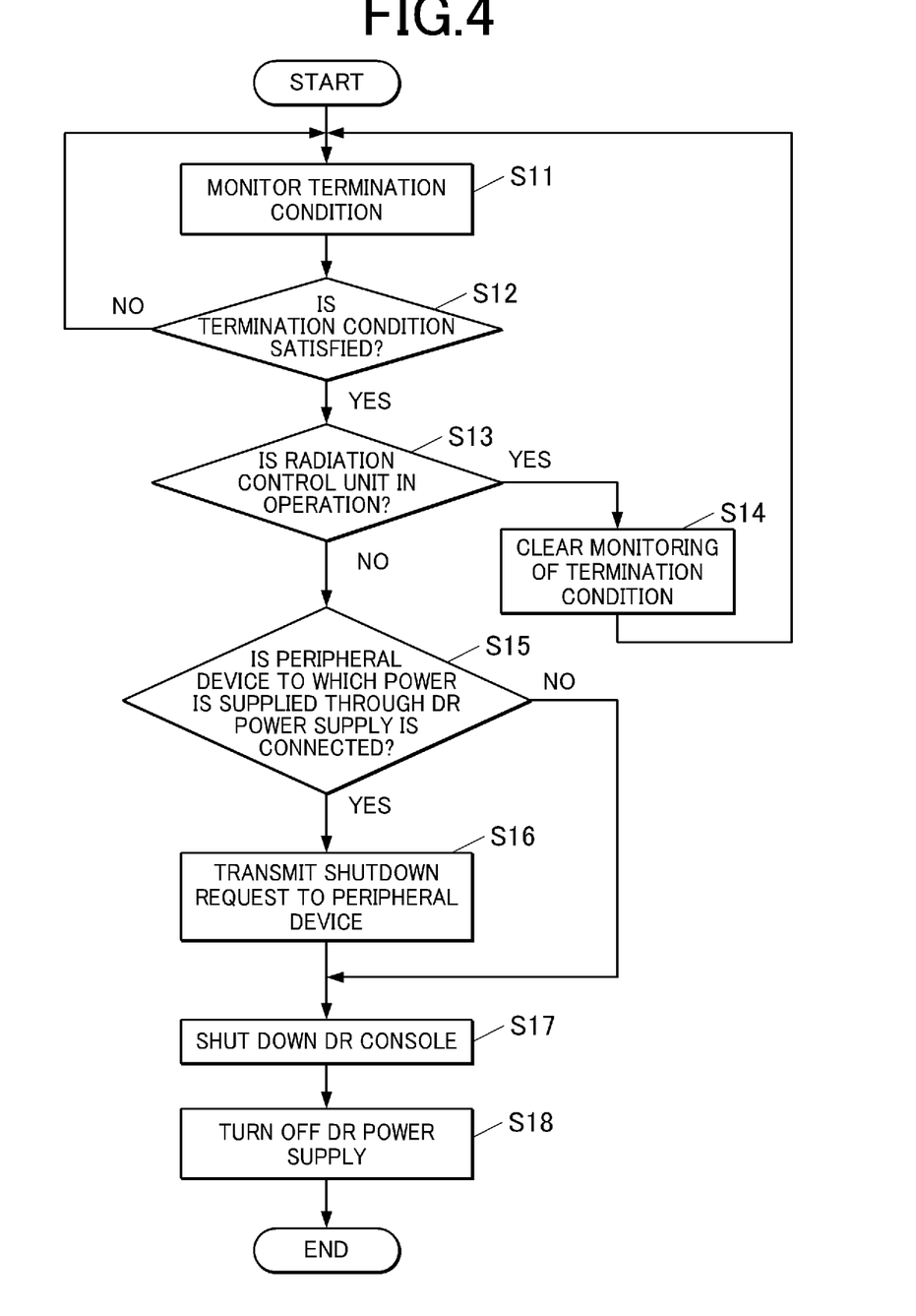
FIG. 4 is a flowchart showing first shutdown determination processing performed in a DR console.

FIG. 4 is a flowchart showing first shutdown determination processing performed in the DR console 21. This processing is performed by cooperation between the CPU of the DR controller 22 and a program stored in the ROM.

First, the DR controller 22 monitors the termination condition of the DR console 21 (step S11), and determines whether or not the termination condition of the DR console 21 is satisfied (step S12).

(Termination Condition A)

For example, the DR controller 22 determines whether or not a state in which no operation (through operation interface 24) has been performed on the DR console 21 continues for a predetermined time or longer. The DR controller 22 determines that the termination condition of the DR console 21 is satisfied when a state in which no operation has been performed on the DR console 21 continues for a predetermined time or longer. If the predetermined time (automatic shutdown waiting time) can be set by the user, the predetermined time can be optimized according to the operation of the facility, thereby improving the convenience.

(Termination Condition B)

The DR controller 22 determines whether or not a termination request has been received from the radiation control unit 11 (or apparatus main power supply 10) through the second communicator 26. The DR controller 22 determines that the termination condition of the DR console 21 is satisfied when a termination request is received from the radiation control unit 11 (or apparatus main power supply 10). For example, a case is assumed in which, when the radiation control unit 11 is forcibly terminated, a termination request is transmitted to the DR console 21 immediately before the radiation control unit 11 is shut down.

(Termination Condition C)

The DR controller 22 determines whether or not a predetermined time or a predetermined time zone has come. The DR controller 22 determines that the termination condition of the DR console 21 is satisfied when a predetermined time or a predetermined time zone comes. If the predetermined time or the predetermined time zone can be set by the user, the predetermined time or the predetermined time zone can be optimized according to the operation of the facility, thereby improving the convenience. For example, by setting the predetermined time or the predetermined time zone according to the facility's normal closing time, automatic shutdown is performed at the closing time. Therefore, it is possible to prevent forgetting to shut down at the time of closing for the day.

(Termination Condition D)

If there is a module in communication in the mobile radiographic imaging apparatus 100, the DR controller 22 determines whether or not this communication has been completed. The DR controller 22 determines that the termination condition of the DR console 21 is satisfied when the communication in the module in communication has been completed. The "module in communication" may include not only a module currently in communication but also a communication module in preparation for communication that is not in communication but has data to be communicated. The "module in communication" includes the first communicator 25 that performs communication between the DR console 21 and an external device, the first communicator 25 that performs communication between the DR console 21 and the FPD 51, and the second communicator 26 that performs communication between the DR console 21 and the radiation control unit 11. It may be determined that the termination condition of the DR console 21 is satisfied when the communication of all communicating modules of these plurality of communicators has been completed, or the completion of communication of communicating modules of some communicators may be a target of communication completion waiting.

For example, a communicator that handles the transmission of an image for diagnosis or an image used for generating an image for diagnosis (for example, first communicator 25 that performs communication between DR console 21 and external device and first communicator 25 that performs communication between DR console 21 and FPD 51) may be set as a target, and a communicator that does not handle the transmission of an image for diagnosis or an image used for generating an image for diagnosis (for example, second communicator 26 that performs communication between DR console 21 and radiation control unit 11) may be set as a non-target, and it may be determined that the termination condition of the DR console 21 is satisfied when the communication of the target communicator is completed. Images have a large amount of data. For this reason, if the transmission of an image is ended during communication, it takes time to transmit the image again when the system restarts. Therefore, it is possible to improve the work efficiency as described above. In addition, by excluding a communicator that does not transmit an image for diagnosis from targets of communication completion waiting, it is possible to prevent a situation in which the termination condition is not easily satisfied due to communication that is not important for the user (for example, state notification between devices) and the remaining battery power is reduced.

Instead of classifying communicators into targets and non-targets of communication completion waiting, the communicators may be classified into targets and non-targets of communication completion waiting according to the content of communication. A "module in communication" related to the transmission of an image for diagnosis or an image used for generating an image for diagnosis may be set as a target of communication completion waiting, and other communicators may be set as non-targets of communication completion waiting. Also in this case, the same effect can be expected.

Alternatively, communicators may be classified into targets and non-targets of communication completion waiting based on the combination of a communicator and the content of communication. Specifically, the first communicator 25 that performs communication between the DR console 21 and an external device is set as a target of communication completion waiting only when the content of communication relates to the transmission of an image for diagnosis or an image used for generating an image for diagnosis, and the others are set as non-targets of communication completion waiting.

Alternatively, communicators may be classified into targets and non-targets of communication completion waiting according to the communication method of each communicator. Specifically, the first communicator 25 that performs wireless LAN communication is set as a non-target of communication completion waiting, and the first communicator 25 that performs wired LAN communication is set as a target of communication completion waiting. In order for the mobile radiographic imaging apparatus 100 to perform wired LAN communication, the user needs to intentionally connect a wired LAN cable to the mobile radiographic imaging apparatus 100. This can be regarded as the user's desire to perform transmission and reception through the wired LAN. For this reason, executing shutdown during wired LAN communication is against the user's intention, which causes inconvenience. Therefore, setting the wired LAN communication as a target of communication completion waiting matches the user's intention.

Conversely, wired LAN communication may be set as a non-target of communication completion waiting, and wireless LAN communication may be set as a target of communication completion waiting. When moving the mobile radiographic imaging apparatus 100 immediately, the user does not connect a wired LAN cable to this apparatus. Therefore, connecting the wired LAN cable to this apparatus can be regarded as not using the mobile radiographic imaging apparatus 100 for a while thereafter. By setting the wireless LAN communication as a target of communication completion waiting and the wired LAN communication as a non-target of communication completion waiting, the communication completion waiting is not performed when the wireless LAN is switched to the wired LAN. Therefore, since it is possible to quickly execute shutdown in anticipation that the apparatus will not be used afterward, it is possible to suppress battery consumption.

Alternatively, communicators may be classified into targets and non-targets of communication completion waiting based on the combination of two or more of a communicator, a communication method of a communicator, and the content of communication. For example, assuming that wireless LAN communication is a target of communication completion waiting and a case where the communication method is wired LAN communication and the content of communication is image transmission is a target of communication completion waiting, it is possible to achieve both the execution of shutdown immediately after connection of a wired LAN cable in anticipation of non-use thereafter and intentional avoidance of shutdown during transmission and reception.

(Termination Condition E)

The DR controller 22 determines whether or not the communication network N between the DR console 21 and an external device has been disconnected. The DR controller 22 determines that the termination condition of the DR console 21 is satisfied when the communication network N between the DR console 21 and the external device is disconnected.

(Termination Condition F)

The mobile radiographic imaging apparatus 100 includes a sensor that detects whether or not there is a person within a predetermined distance from the DR console 21.

The DR controller 22 determines whether or not there is no user in front of the DR console 21 for a predetermined time based on the output signal of the sensor. The DR controller 22 determines that the termination condition of the DR console 21 is satisfied when there is no user in front of the DR console 21 for a predetermined time. "There is no user in front of the DR console 21" is considered that the DR console 21 is not in use.

User identification such as face recognition may be performed depending on the type of sensor, and it may be determined that the termination condition is satisfied (there is no user for a predetermined time) when there is a person in front of the DR console 21 who is not suitable as a user.

(Termination Condition G)

The DR controller 22 determines that the termination condition of the DR console 21 is satisfied when all scheduled examinations in round imaging among the pieces of examination order information issued from the RIS 110 for the DR console 21 are completed or when a predetermined time or more has passed after the completion. The completion of examinations may be triggered by communication with an external device by the communication module described in the termination condition D, that is, completion of image output.

(Termination Condition H)

The DR controller 22 determines that the termination condition of the DR console 21 is satisfied when a predetermined time or more has passed after a predetermined number of used FPDs 51 are stored in the panel storage space attached to the mobile radiographic imaging apparatus 100. The state in which the FPD 51 is stored is determined to be a state in which imaging is not performed, and is regarded as a state in which the DR console 21 is not in use.

As the termination condition of the DR console 21, a combination of a plurality of conditions may be used. For example, the termination condition A and the termination condition C may be combined in such a manner that a time zone during which automatic shutdown is effective (for example, nighttime) is set in the termination condition C and the automatic shutdown is performed only when a state in which no operation (through operation interface 24) has been performed on the DR console 21 continues for a predetermined time or longer during the time zone. In this case, in a time zone during which the mobile radiographic imaging apparatus 100 is used frequently (for example, daytime), automatic shutdown is not performed. Therefore, the user can use the mobile radiographic imaging apparatus 100 immediately when the user desires to use the mobile radiographic imaging apparatus 100. In a time zone during which the mobile radiographic imaging apparatus 100 is used less frequently (for example, nighttime), it is possible to perform automatic shutdown by prioritizing battery life. Generally, there are few users in the facility at night. Therefore, a user who is not familiar with using the mobile radiographic imaging apparatus 1100 is expected to use the apparatus. For this reason, there is a possibility that the user forgets to shut down the apparatus. In the manner described above, it is possible to avoid such a situation.

If the termination condition of the DR console 21 is not satisfied in step S12 (step S12; NO), the process returns to step S11 to repeat the processing.

If the termination condition of the DR console 21 is satisfied in step S12 (step S12; YES), the DR controller 22 determines whether or not the radiation control unit 11 is in operation (step S13).

Specifically, the DR controller 22 inquires of the radiation control unit 11, through the second communicator 26, about whether or not the radiation control unit 11 is in operation.

When the radiation control unit 11 is in operation, the main controller 12 of the radiation control unit 11 transmits a response indicating that the radiation control unit 11 is in operation to the DR console 21 through the communicator 17.

When the DR controller 22 receives the response indicating that the radiation control unit 11 is in operation through the second communicator 26, the DR controller 22 determines that the radiation control unit 11 is in operation.

On the other hand, when there is no response from the radiation control unit 11, the DR controller 22 determines that the radiation control unit 11 is not in operation.

If the radiation control unit 11 is in operation in step S13 (step S13; YES), the DR controller 22 clears the monitoring of the termination condition (step S14). That is, the DR controller 22 redefines a state in which the termination condition of the DR console 21 is satisfied.

After step S14, the process returns to step S11 to repeat the processing.

If the radiation control unit 11 is not in operation in step S13 (step S13; NO), that is, if the radiation control unit 11 has already been shut down and the apparatus main power supply 10 is turned off, the DR controller 22 proceeds to step S15 to start the termination sequence of the DR console 21.

The DR controller 22 determines whether or not a peripheral device, to which power is supplied through the DR power supply 20, is connected to the DR console 21 (step S15). Specifically, the DR controller 22 determines whether or not the exposure interlocking unit 41 or the FPD 51 are connected as a peripheral device to which power is supplied through the DR power supply 20. The peripheral device may also be an access point or the like to which power is supplied through the DR power supply 20.

If a peripheral device to which power is supplied through the DR power supply 20 is connected (step S15; YES), the DR controller 22 transmits a shutdown request to the peripheral device (step S16).

The peripheral device (exposure interlocking unit 41, FPD 51, and the like) that has received the shutdown request shuts down itself to cut off the supply of power from the DR power supply 20 to the peripheral device.

After step S16 or if a peripheral device to which power is supplied through the DR power supply 20 is not connected in step S15 (step S55; NO), the DR controller 22 shuts down the DR console 21 (step S17), and turns off the DR power supply 20 (step S18).

As described above, the first shutdown determination processing ends.

As described above, according to the first embodiment, the DR controller 22 of the DR console 21 inquires of the radiation control unit 11 about the state of the radiation control unit 11 when the termination condition (predetermined condition) of the DR console 21 is satisfied, and shuts down the DR console 21 or cancels the shutdown of the DR console 21 according to the response from the radiation control unit 11. The DR controller 22 can determine whether or not this is time to shut down the DR console 21 based on the termination condition of the DR console 21, and can determine whether or not to shut down the DR console 21 in consideration of the state of the radiation control unit 11. Since the DR controller 22 automatically determines the termination condition of the DR console 21, an instruction through the user's operation or the like is not necessary. In addition, the DR controller 22 checks the state of the radiation control unit 11 to prevent any problem from occurring in the entire apparatus. Therefore, in the mobile radiographic imaging apparatus 100 having two independent power supply units (apparatus main power supply 10 and DR power supply 20), it is possible to achieve both efficient power consumption and user's convenience. In addition, by shutting down the DR console 21, patient information or captured images are not displayed. Therefore, privacy can be protected.

For example, when a state in which no operation has been performed on the DR console 21 continues for a predetermined time or longer, the DR controller 22 of the DR console 21 shuts down the DR console 21 and terminates the DR power supply 20. Therefore, the non-use state of the DR console 21 can be used as a trigger for shutting down the DR console 21 itself.

As shown in step S16 of the first shutdown determination processing (see FIG. 4), the DR controller 22 of the DR console 21 transmits a shutdown request to a peripheral device connected to the DR console 21 before shutting down the DR console 21, so that it is possible to prevent the peripheral device from continuing to operate after the DR console 21 is shut down.

If "completion of communication between the DR console 21 and the external device" is used as the termination condition in step S12 of the first shutdown determination processing, the shutdown of the DR console 21 and the turning off of the DR power supply 20 are not performed while the communication between the DR console 21 and the external device continues (step S12; NO).

Instead of waiting until the termination condition is satisfied, the DR controller 22 of the DR console 21 may not shut down the DR console 21 (turn off DR power supply 20) or may postpone the shutdown of the DR console 21 (turning off of DR power supply 20) while the communication between the DR console 21 and the external device continues. As communication between the DR console 21 and the external device, a case of transmitting a large-sized image, such as a dynamic image, to the PACS 120 or the dynamic analysis device 130 is assumed.

Similarly, the DR controller 22 of the DR console 21 may not shut down the DR console 21 (turn off DR power supply 20) or may postpone the shutdown of the DR console 21 (turning off of DR power supply 20) when at least one of an operation on the operation interface 53 of the FPD 51 and attachment/detachment of a cable connecting the FPD 51 and the exposure interlocking unit 41 (while switching between wired communication and wireless communication for FPD 51) occurs.

Alternatively, the DR controller 22 of the DR console 21 may not shut down the DR console 21 (turn off DR power supply 20) or may postpone the shutdown of the DR console 21 (turning off of DR power supply 20) when the mobile radiographic imaging apparatus 100 is in a charging state, that is, when the battery 30 is connected to the external power supply 35.

The DR controller 22 of the DR console 21 may shift the DR console 21 to a sleep state when the mobile radiographic imaging apparatus 100 is in a charging state.

The DR controller 22 of the DR console 21 may shift the display 23 of the DR console 21 to an off state (blackout) when the mobile radiographic imaging apparatus 100 is in a charging state.

First Modification Example

Next, a first modification example of the first embodiment will be described. The following description will be focused on differences from the first embodiment.

Figure 5:
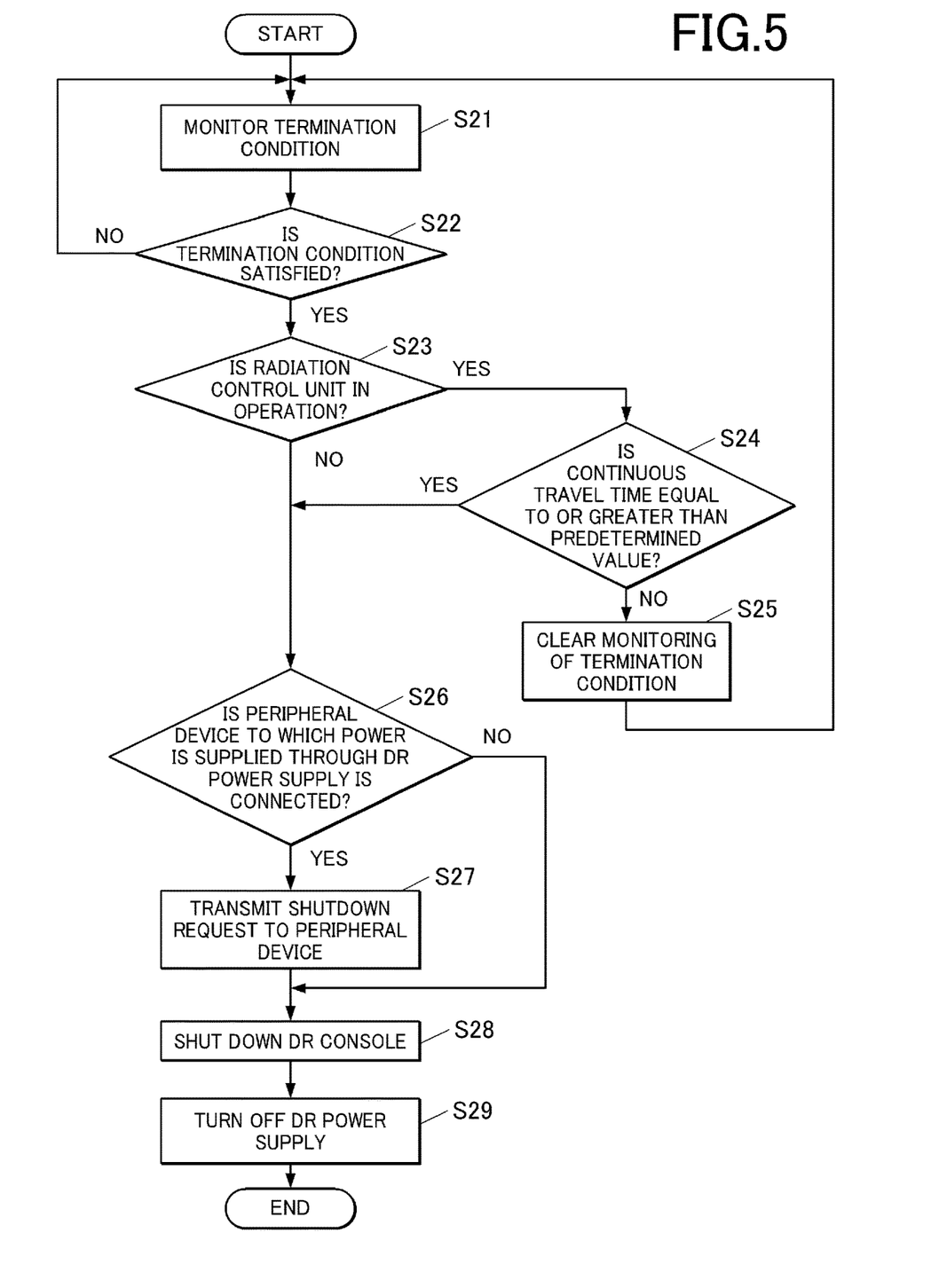
FIG. 5 is a flowchart showing second shutdown determination processing performed in a DR console of a first modification example.

In the first modification example, when the termination condition of the DR console 21 is satisfied, not only whether or not the radiation control unit 11 is in operation but also the continuous travel time of the mobile radiographic imaging apparatus 100 is used as the content of the inquiry from the DR console 21 to the radiation control unit 11.

FIG. 5 is a flowchart showing second shutdown determination processing performed in the DR console 21. This processing is performed by cooperation between the CPU of the DR controller 22 and a program stored in the ROM.

The processing of steps S21 to S23 is the same as the processing of steps S11 to S13 in the first shutdown determination processing (see FIG. 4), and accordingly, the explanation thereof will be omitted.

If the radiation control unit 11 is in operation in step S23 (step S23; YES), the DR controller 22 determines whether or not the continuous travel time of the mobile radiographic imaging apparatus 100 is equal to or greater than a predetermined value. (step S24). This determination is based on the idea that radiographic imaging is not performed while the mobile radiographic imaging apparatus 100 is traveling (moving).

Specifically, the DR controller 22 inquires of the radiation control unit 11, through the second communicator 26, about whether or not the traveling by the driver 14 continues for a predetermined time or longer.

The main controller 12 of the radiation control unit 11 transmits a response to the DR console 21 through the communicator 17 as to whether or not the traveling by the driver 14 continues for a predetermined time or longer.

Based on the response from the radiation control unit 11 that has been received through the second communicator 26, the DR controller 22 determines whether or not the continuous travel time of the mobile radiographic imaging apparatus 100 is equal to or greater than a predetermined value.

When the DR controller 22 inquires of the radiation control unit 11 about whether or not the mobile radiographic imaging apparatus 100 is "traveling" and the response from the radiation control unit 11 indicates that the state of "traveling" continues a predetermined number of times or more, the DR controller 22 may determine that the continuous travel time of the mobile radiographic imaging apparatus 100 is equal to or greater than the predetermined value.

If the continuous travel time of the mobile radiographic imaging apparatus 100 is less than the predetermined value in step S24 (step S24; NO), the DR controller 22 clears the monitoring of the termination condition (step S25), and returns to step S21 to repeat the processing.

If the radiation control unit 11 is not in operation in step S23 (step S23; NO) or if the continuous travel time of the mobile radiographic imaging apparatus 100 is equal to or greater than the predetermined value in step S24 (step S24; YES), the DR controller 22 proceeds to step S26 to start the termination sequence of the DR console 21.

The processing of steps S26 to S29 is the same as the processing of steps S15 to S18 in the first shutdown determination processing (see FIG. 4), and accordingly, the explanation thereof will be omitted.

As described above, the second shutdown determination processing ends.

According to the first modification example, in addition to the same effect as in the first embodiment, if the termination condition of the DR console 21 is satisfied, it is possible to shut down the DR console 21 and terminate the DR power supply 20 when the continuous travel time of the mobile radiographic imaging apparatus 100 is equal to or greater than the predetermined value even if the radiation control unit 11 is in operation. That is, when the mobile radiographic imaging apparatus 100 is traveling (moving), it is assumed that radiographic imaging will not be performed immediately. Therefore, it is possible to reduce power consumption by shutting down the DR console 21.

Second Modification Example

Next, a second modification example of the first embodiment will be described. The following description will be focused on differences from the first embodiment.

Figure 6:
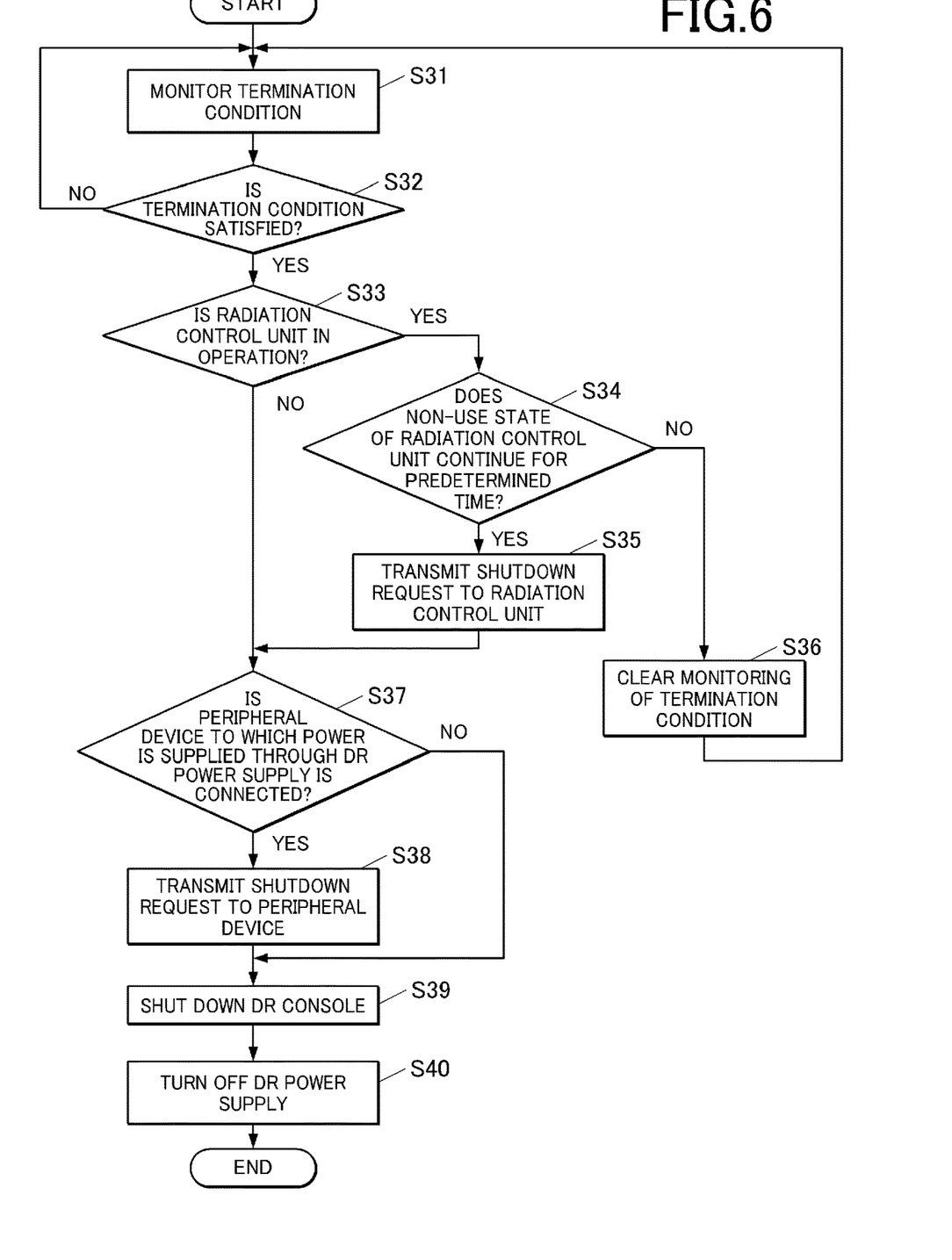
FIG. 6 is a flowchart showing third shutdown determination processing performed in a DR console of a second modification example.

In the second modification example, when the termination condition of the DR console 21 is satisfied, not only whether or not the radiation control unit 11 is in operation but also the non-use state of the radiation control unit 11 is used as the content of the inquiry from the DR console 21 to the radiation control unit 11.

FIG. 6 is a flowchart showing third shutdown determination processing performed in the DR console 21. This processing is performed by cooperation between the CPU of the DR controller 22 and a program stored in the ROM.

The processing of steps S31 to S33 is the same as the processing of steps S11 to S13 in the first shutdown determination processing (see FIG. 4), and accordingly, the explanation thereof will be omitted.

If the radiation control unit 11 is in operation in step S33 (step S33; YES), the DR controller 22 determines whether or not the non-use state of the radiation control unit 11 (radiation emission function, movement/traveling function, and the like) continues for a predetermined time (step S34).

Specifically, the DR controller 22 inquires of the radiation control unit 11, through the second communicator 26, about the output voltage value of the apparatus main power supply 10 as a use state of the radiation control unit 11.

The main controller 12 of the radiation control unit 11 transmits the output voltage value of the apparatus main power supply 10 to the DR console 21 through the communicator 17.

The DR controller 22 determines whether or not the radiation control unit 11 is being used based on the output voltage value of the apparatus main power supply 10 received from the radiation control unit 11. The DR controller 22 determines that the radiation control unit 11 is in a non-use state when the output voltage value of the apparatus main power supply 10 is equal to or less than a predetermined value.

The DR controller 22 repeats inquiry to the radiation control unit 11 to determine whether or not the non-use state of the radiation control unit 11 continues for a predetermined time.

If the non-use state of the radiation control unit 11 continues for a predetermined time in step S34 (step S34; YES), the DR controller 22 transmits a shutdown request to the radiation control unit 11 through the second communicator 26 (step S35).

When the radiation control unit 11 receives the shutdown request through the communicator 17, the main controller 12 shuts down the radiation control unit 11 and turns of the apparatus main power supply 10 based on the shutdown request.

If the non-use state of the radiation control unit 11 does not continue for the predetermined time in step S34 (step S34; NO), the DR controller 22 clears the monitoring of the termination condition (step S36), and returns to step S31 to repeat the processing.

If the radiation control unit 11 is not in operation in step S33 (step S33; NO) or after step S35, the process proceeds to step S37. That is, when the radiation control unit 11 has already been shut down and the apparatus main power supply 10 is turned off or when the radiation control unit 11 is expected to be shut down due to a shutdown request to the radiation control unit 11, the DR controller 22 starts the termination sequence of the DR console 21.

The processing of steps S37 to S40 is the same as the processing of steps S15 to S18 in the first shutdown determination processing (see FIG. 4), and accordingly, the explanation thereof will be omitted.

As described above, the third shutdown determination processing ends.

According to the second modification example, in addition to the same effect as in the first embodiment, if the termination condition of the DR console 21 is satisfied, it is possible to shut down the DR console 21 and terminate the DR power supply 20 when the non-use state of the radiation control unit 11 continues for a predetermined time or longer even if the radiation control unit 11 is in operation. That is, when the radiation control unit 11 is not in use, it is assumed that radiographic imaging will not be performed immediately. Therefore, it is possible to reduce power consumption by shutting down the DR console 21.

As shown in step S35 of the third shutdown determination processing (see FIG. 6), the DR controller 22 of the DR console 21 transmits a shutdown request to the radiation control unit 11 before shutting down the DR console 21, so that it is possible to suppress power consumption in the radiation control unit 11 when the radiation control unit 11 is not in use.

In the third shutdown determination processing, when shutting down the DR console 21, if the non-use state of the radiation control unit 11 continues for a predetermined time, a shutdown request is transmitted to the radiation control unit 11. However, regardless of the timing of shutting down the DR console 21, when a state in which the radiation control unit 11 is not used and only the DR console 21 is continuously operated for a predetermined time continues for a predetermined time, a shutdown request may be transmitted from the DR console 21 to the radiation control unit 11.

Third Modification Example

Next, a third modification example of the first embodiment will be described. The following description will be focused on differences from the first embodiment.

Figure 7:
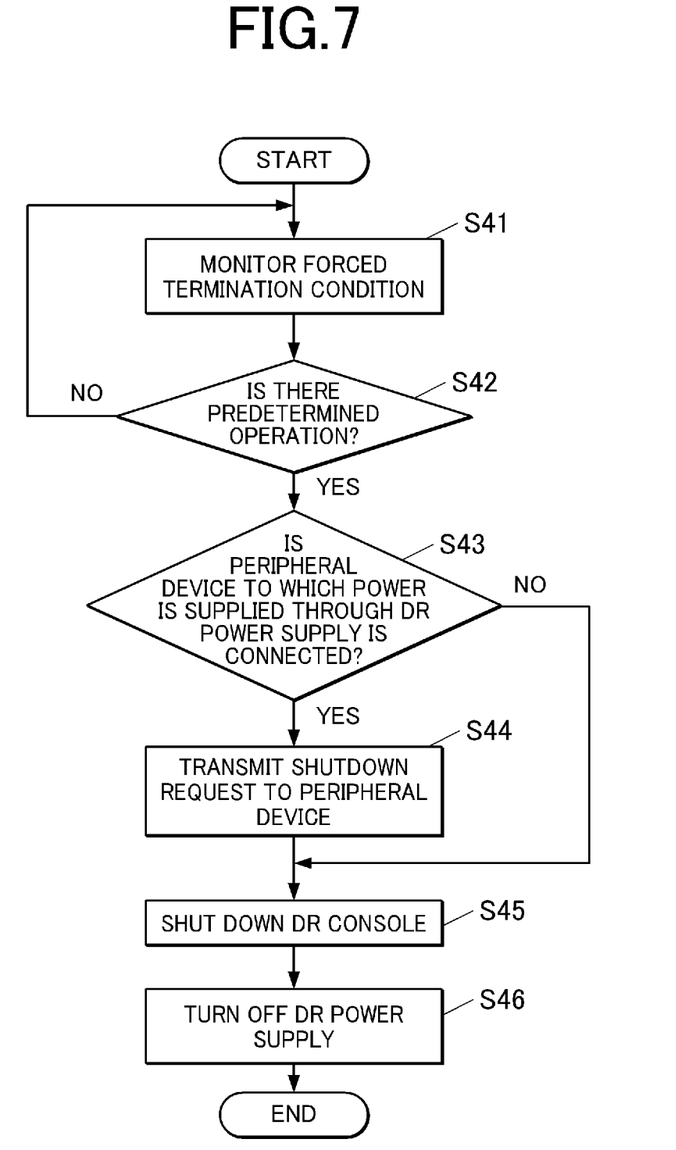
FIG. 7 is a flowchart showing fourth shutdown determination processing performed in a DR console of a third modification example.

In the third modification example, when the forced termination condition of the DR console 21 is satisfied, the DR console 21 is shut down without making an inquiry from the DR console 21 to the radiation control unit 11.

FIG. 7 is a flowchart showing fourth shutdown determination processing performed in the DR console 21. This processing is performed by cooperation between the CPU of the DR controller 22 and a program stored in the ROM.

First, the DR controller 22 monitors the forced termination condition of the DR console 21 (step S41), and determines whether or not the user has performed a predetermined operation (operation corresponding to forced termination condition) on the DR console 21 (step S42). The predetermined operation is not limited to an operation on the operation interface 24.

Examples of the predetermined operation corresponding to the forced termination conditions include the pressing of a shutdown button, an operation by voice control, and a remote operation from a device capable of communicating with the DR console 21.

If there is no predetermined operation in step S42 (step S42; NO), the process returns to step S41 to repeat the processing.

If there is a predetermined operation in step S42 (step S42; YES), the process proceeds to step S43. That is, the DR controller 22 starts the termination sequence of the DR console 21 without inquiring of the radiation control unit 11 about the state of the radiation control unit 11.

The processing of steps S43 to S46 is the same as the processing of steps S15 to S18 in the first shutdown determination processing (see FIG. 4), and accordingly, the explanation thereof will be omitted.

As described above, the fourth shutdown determination processing ends.

According to the third modification example, it is possible to forcibly terminate the DR console 21 by performing a predetermined operation. The timing of forced termination may be, for example, when the battery 30 is likely to run out before the mobile radiographic imaging apparatus 100 is completely moved to the target location.

In the first embodiment and its first to third modification examples, the case has been described in which the DR console 21 is "one control device" and the radiation control unit 11 is "the other control device". However, the present invention is not limited to this. The radiation control unit 11 side may inquire of the DR console 21 about the state of the DR console 21 when the termination condition of the radiation control unit 11 is satisfied.

Second Embodiment

Next, a second embodiment to which the present invention is applied will be described.

Since a mobile radiographic imaging apparatus according to the second embodiment has the same configuration as the mobile radiographic imaging apparatus 100 according to the first embodiment, FIGS. 1 and 2 are referred to and the illustration and description of the configuration will be omitted. Hereinafter, the characteristic configuration and processing of the second embodiment will be described.

In the second embodiment, in the mobile radiographic imaging apparatus 100, both the radiation control unit 11 and the DR console 21 (two control devices) have their own termination conditions. That is, each of the radiation control unit 11 and the DR console 21 has a function of determining whether or not its own termination condition is satisfied and shutting down itself and terminating a power supply unit (apparatus main power supply 10 and DR power supply 20) corresponding to the control device itself when the termination condition is satisfied (hereinafter, referred to as an "automatic shutdown function").

In the second embodiment, instead of a control device that satisfies the termination condition inquiring of the other control device about the state of the other control device, a control device to be shut down notifies the other control device that itself will be shut down and then shuts itself down.

Figure 8:
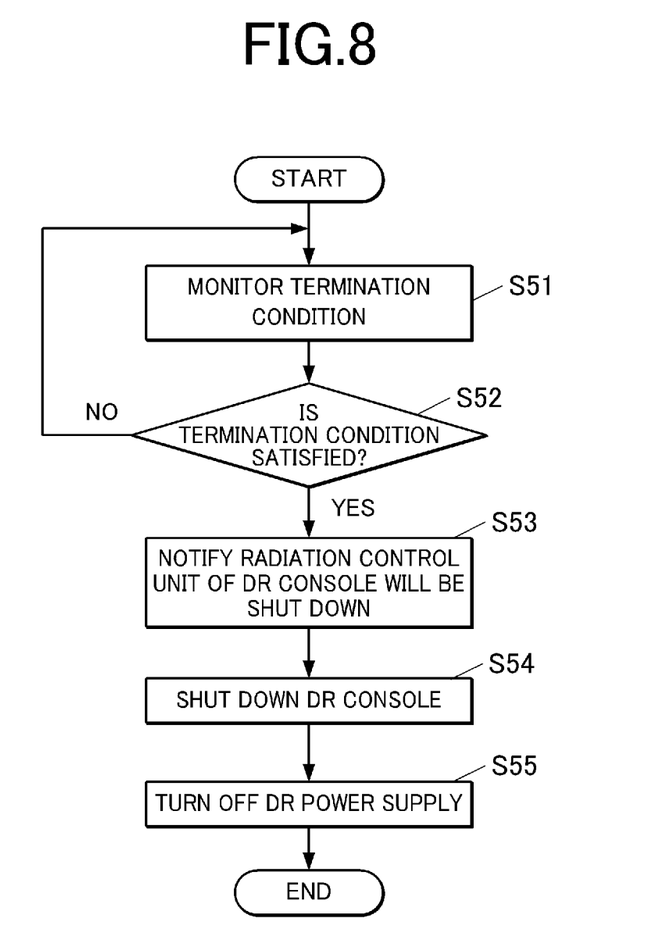
FIG. 8 is a flowchart showing fifth shutdown determination processing performed in a DR console according to a second embodiment.

FIG. 8 is a flowchart showing fifth shutdown determination processing performed in the DR console 21. This processing is performed by cooperation between the CPU of the DR controller 22 and a program stored in the ROM.

The processing of steps S51 and S52 is the same as the processing of steps S11 and S12 in the first shutdown determination processing (see FIG. 4), and accordingly, the explanation thereof will be omitted.

If the termination condition of the DR console 21 is satisfied in step S52 (step S52; YES), the DR controller 22 notifies the radiation control unit 11 through the second communicator 26 that the DR console 21 will be shut down (step S53).

Then, the DR controller 22 shuts down the DR console 21 (step S54), and turns off the DR power supply 20 (step S55).

As described above, the fifth shutdown determination processing ends.

Although the processing on the DR console 21 side has been described in the fifth shutdown determination processing, the same applies to the radiation control unit 11 as well. Specifically, the main controller 12 of the radiation control unit 11 determines the timing of shutting down the radiation control unit 11 based on the termination condition of the radiation control unit 11. Then, before shutting down the radiation control unit 11, the main controller 12 notifies the DR console 21 through the communicator 17 that the radiation control unit 11 will be shut down.

As described above, according to the second embodiment, each of the radiation control unit 11 and the DR console 21 determines the timing of shutting down itself based on its own termination condition. Therefore, in the mobile radiographic imaging apparatus 100 having two independent power supply units, it is possible to achieve both efficient power consumption and user's convenience.

In the mobile radiographic imaging apparatus 100 in which both the radiation control unit 11 and the DR console 21 have an automatic shutdown function, the radiation control unit 11 can shut down the radiation control unit 11 (terminate apparatus main power supply 10) regardless of the state of the DR console 21. However, only when at least the apparatus main power supply 10 is off and there is no operation on the DR console 21, shutdown of the DR console 21 (termination of DR power supply 20) may be enabled. Therefore, it is possible to avoid automatic shutdown of the DR console 21 when the DR console 21 is not operated for a predetermined time, such as when the mobile radiographic imaging apparatus 100 is traveling, but there is a possibility that the DR console 21 will be used shortly thereafter.

In the mobile radiographic imaging apparatus 100 in which both the radiation control unit 11 and the DR console 21 (two control devices) have an automatic shutdown function, the automatic shutdown settings (termination condition and the like) stored in each control device can be copied from one control device to the other control device. This eliminates the need for the user to perform automatic shutdown settings for each of the two control devices. In addition, convenience can be improved by allowing automatic shutdown settings to be performed from the DR console 21 side, which has a full user interface.

The automatic shutdown settings that can be copied include, for example, an automatic shutdown waiting time in the termination condition A. When the radiation control unit 11 side also has an automatic shutdown execution determination function based on the automatic shutdown waiting time, that is, when the main controller 12 determines whether or not a state in which there is no operation on the radiation control unit 1I through the operation interface 16 of the radiation control unit 11 continues for a predetermined time or longer and the radiation control unit 11 has a function of determining that the termination condition of the radiation control unit 11 is satisfied when the state in which there is no operation on the radiation control unit 11 continues for the predetermined time or longer, the automatic shutdown waiting time on the DR console 21 side may be transmitted to the radiation control unit 11 through communication between the second communicator 26 of the DR console 21 and the communicator 17 of the radiation control unit 11, and the value may be stored (copied) and used by the radiation control unit 11. As a standard workflow for ending the use of the mobile radiographic imaging apparatus 100, the mobile radiographic imaging apparatus 100 is moved to a place where this is not used by operating the operation interface 16 (for example, handlebar for traveling) of the radiation control unit 11, and after arriving at the place, whether or not there is any image to be transmitted from the first communicator 25 to the PACS 120 or the like is checked by operating the operation interface 24 of the DR console 21. Thereafter, the radiation generator 13 is moved to the storage location by operating the operation interface 16 of the radiation control unit 11, thereby ending a series of operations. Thus, since the last operation on the radiation control unit 11 and the last operation on the DR console 21 side are generally at the same timing, if the automatic shutdown waiting time for both is made to be the same by copying, the timing of automatic shutdown on the radiation control unit 11 side and the timing of automatic shutdown on the DR console 21 side are generally the same in many cases. If the timing of automatic shutdown on the radiation control unit 11 side and the timing of automatic shutdown on the DR console 21 side are greatly different, the user becomes uneasy about whether or not the automatic shutdown functions normally. Accordingly, there will be cases where a manual shutdown operation is performed, which reduces the user's convenience. However, if the timing of automatic shutdown on the radiation control unit 11 side and the timing of automatic shutdown on the DR console 21 side are approximately the same as described above, the manual shutdown operation is unnecessary, which improves convenience.

The description in each of the above embodiments and its modification examples are examples of the mobile radiographic imaging apparatus according to the present invention, and the present invention is not limited thereto. The detailed configuration and detailed operation of each unit of the apparatus can be appropriately changed without departing from the spirit of the present invention.

For example, in each of the above-described embodiments and its modification examples, the radiation control unit 11 controls functional units related to radiation emission and operations for driving the mobile radiographic imaging apparatus 100, and the DR console 21 controls functional units related to radiation emission and operations on captured images. However, the division of roles between the two control devices in the mobile radiographic imaging apparatus 100 (what functional unit is to be controlled) is not limited to this example.

When starting the processing for shutting down the DR console 21 and turning off the DR power supply 20, the user may be notified of the shutdown of the DR console 21 and turning off of the DR power supply 20 by some means (dialogue display, sound, light, and the like).

Similarly, when starting the processing for shutting down the radiation control unit 11 and turning off the apparatus main power supply 10, the user may be notified.

In the DR console 21 or the radiation control unit 11, a time zone during which it is determined whether or not the termination condition is satisfied may be set in advance. For example, it is possible to avoid automatic shutdown during the daytime by allowing the determination as to whether or not the termination condition is satisfied only at nighttime.

The present invention can be applied regardless of whether or not the mobile radiographic imaging apparatus 100 is connected to the external power supply 35. However, since it is not necessary to consider saving the battery 30 while the mobile radiographic imaging apparatus 100 is connected to the external power supply 35 (while the mobile radiographic imaging apparatus 100 is being charged), the present invention is particularly effective in a situation in which the mobile radiographic imaging apparatus 100 is not connected to the external power supply 35.

A program for executing each process may be stored in a portable recording medium or the like. A carrier wave may be applied as a medium for providing program data through a communication line.

As for the automatic shutdown function in the present invention, the termination condition or whether or not to execute the automatic shutdown function may be set for each mobile radiographic imaging apparatus 100, each facility, and each logged-in user.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A mobile radiographic imaging apparatus, comprising:
two independent power supply units;
two control devices each being driven with power supplied from each of the two power supply units;
a first hardware processor in one of the two control devices includes; and
a second hardware processor in the other one of the two control device, wherein
the first hardware processor inquires of the second hardware processor about a state of the other control device when a predetermined condition is satisfied, and shuts down the one control device or cancels shutdown of the one control device according to a response from the other control device.

2. The mobile radiographic imaging apparatus according to claim 1,
wherein the first hardware processor transmits a shutdown request to the other control device or a peripheral device connected to the one control device before shutting down the one control device.

3. The mobile radiographic imaging apparatus according to claim 1,
wherein the predetermined condition is that a state in which no operation has been performed on the one control device continues for a predetermined time or longer.

4. The mobile radiographic imaging apparatus according to claim 1,
wherein the one control device controls functional units related to radiation detection and an operation on a captured image, and
the other control device controls functional units related to radiation emission and an operation for driving the mobile radiographic imaging apparatus.

5. A control method for a mobile radiographic imaging apparatus including two independent power supply units and two control devices each being driven with power supplied from each of the two power supply units, the method comprising:
causing a first hardware processor of one of the two control devices to inquire of a second hardware processor of the other one of the two control devices about a state of the other control device when a predetermined condition is satisfied and to shut down the one control device or cancel shutdown of the one control device according to a response from the other control device.

6. A non-transitory recording medium storing a computer readable program causing a computer of one of two control devices of a mobile radiographic imaging apparatus including two independent power supply units and the two control devices each being driven with power supplied from each of the two power supply units to execute:
inquiring of the other one of the two control dev ices about a state of the other control device when a predetermined condition is satisfied; and
shutting down the one control device or canceling shutdown of the one control device according to a response from the other control device.

* * * * *